(12) United States Patent
Hein et al.

(10) Patent No.: US 7,010,082 B2
(45) Date of Patent: Mar. 7, 2006

(54) METHOD FOR CONDUCTING A TEST MEASUREMENT IN A CT APPARATUS, AND CT APPARATUS

(75) Inventors: Peter Hein, Bamberg (DE); Helmut Kropfeld, Forchheim (DE); Mario Reinwand, Breitbrunn (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/856,365

(22) Filed: May 28, 2004

(65) Prior Publication Data

US 2005/0002495 A1 Jan. 6, 2005

(30) Foreign Application Priority Data

May 30, 2003 (DE) ................................ 103 24 683

(51) Int. Cl.
*A61B 6/00* (2006.01)
(52) U.S. Cl. ......................................... 378/18; 378/207
(58) Field of Classification Search ................. 378/207, 378/18, 4
See application file for complete search history.

(56) References Cited

U.S. PATENT DOCUMENTS

| 4,352,020 A | * | 9/1982 | Horiba et al. ................. 378/18 |
| 6,470,065 B1 | | 10/2002 | Lauther |
| 6,490,336 B1 | | 12/2002 | Suess et al. |
| 6,508,586 B1 | * | 1/2003 | Oota ........................... 378/196 |

* cited by examiner

*Primary Examiner*—David V. Bruce
*Assistant Examiner*—Hoon Song
(74) *Attorney, Agent, or Firm*—Schiff Hardin LLP

(57) ABSTRACT

In an x-ray computed tomography apparatus and a method for conducting test measurements therein, a combined phantom is employed that is formed of several individual phantoms, each forming a segment of the combined phantom, and the combined phantom is affixed to a platform of the computed tomography apparatus that is movable with respect to an x-ray data acquisition unit of the computed tomography apparatus. The platform is moved into a first position and a first x-ray absorption distribution of a first segment of the combined phantom is obtained, and the platform is moved into a second position and a second x-ray absorption distribution is obtained of a second segment of the phantom. Movement of the platform and operation of the data acquisition unit for obtaining the first and second x-ray distributions are automatically controlled by a computer program.

12 Claims, 2 Drawing Sheets

METHOD FOR CONDUCTING A TEST MEASUREMENT IN A CT APPARATUS, AND CT APPARATUS

BACKGROUND OF THE INVENTION

1. Field of the Invention

The present invention concerns a procedure to carry out test measurements on an X-ray computed tomography apparatus as well as a computed tomography apparatus.

2. Description of the Prior Art

Artificial test specimens are used on X-ray computed tomography (CT) to carry out test measurements and to calibrate or adjust the unit, particularly with respect to adjusting the size of the sampled area. Such test specimens are also called "phantoms". Phantoms contain components of various specific densities in various geometric shapes. For example, a phantom of this type is described in German OS 198 52 324. Calibration of the CT apparatus is done with reference to cross-sectional views of such phantoms.

The required sampling and adjustments or calibration on a CT apparatus can be grouped in the following categories:
 A. Adjustments made daily by the user as part of a regular routine.
 B. Test measurements made by the user as part of a regular routine, perhaps monthly, to test the quality of the measurement results.
 C. Adjustments made by repair personnel after exchanging hardware components, for example.
 D. Adjustments made during construction of the CT.

The adjustments listed above may be related in part, i.e. an adjustment in category C may require a subsequent adjustment in category A.

Most of the specified adjustments and test measurements require that one, and in most instances more than one phantom, be inserted in the CT apparatus in a precise Z-position (the z-axis being parallel to the system axis around which rotation occurs). It may also be necessary to specify certain parameters for each phantom prior to measurement. This procedure is time consuming and requires subject matter knowledge.

A simplification of the procedure has been proposed in a CT apparatus that sends program-controlled prompts to the user. The user instructions lead the service personnel through a pre-determined series of steps to mount the phantom correctly and in the proper Z-position, as well as to enter the parameters required for calibration. The proposed user instructions generally assure that all steps are appropriately made in the correct order. Nonetheless, this procedure is also time consuming.

A further proposal to simplify the procedure replaces the need (if it exists) to use multiple phantom bodies, with a combined phantom. This reduces the time required to exchange and calibrate the various individual phantoms. Nonetheless, the use of a combined phantom still requires mounting it in the CT apparatus in the proper Z-position. Calibration requires the entry of the parameters for the combined phantom in the proper sequence. That is also time consuming and requires subject matter knowledge to some degree.

SUMMARY OF THE INVENTION

An object of the present invention to provide a CT calibration method and apparatus that overcome the limitations in the current state of technology. Specifically, a simplified procedure for test measurements of an X-ray computed tomography apparatus is needed. It is a further goal of the invention to provide for an automatic calibration of a computed tomography apparatus.

This object is achieved in accordance with the invention by a procedure to make test measurements of an X-ray computed tomography apparatus including the steps of providing a combined phantom formed of several individual phantoms, with each phantom forming a segment of the phantom, and affixing the phantom to a platform that is movable with respect to an X-ray/detection unit, moving the platform into a specified first position and obtain a first X-ray absorption distribution in a first segment of the phantom, and moving the platform from the initial position into another specified position and obtaining at least one additional X-ray absorption distribution in at least one additional segment of the phantom, with the movement of the platform, the measurements and the calibration being conducted are handled automatically by a computer program in an order designated by that program.

As used herein a computed tomography apparatus is defined as general units capable of tomography, such for example C-arm X-ray units.

The procedure is simple and can be carried out quickly. Subject matter knowledge is not required. All steps of the procedure are carried out automatically. Intervention by the user is not required. The phantom is moved into the proper test position in each case by the computer program. A cross-sectional view may be obtained in the conventional way from the measured X-ray absorption distribution. A test measurement of the X-ray computed tomography apparatus is particularly useful to determine the proper calibration of the unit. Standard phantoms are measured by the test measurement. The quality of the resulting views identifies at once whether re-calibration of the X-ray computed tomography apparatus is required.

The X-ray/detection unit of an X-ray computed tomography apparatus may be a unit that can rotate 360°, with an X-ray tube attached opposite the detection unit. A platform, which may contain a bed for a patient, is situated opposite the X-ray/detection unit and is adjustable relative to it. The term "platform" is defined in the present invention as any component of a CT apparatus that is movable relative to the X-ray/detection under the control of the computer program and that is suited to support the phantom.

In an embodiment, the computer program issues a prompt prior to the first step to attach the phantom to the platform. The proper mounting of the phantom on the platform can be signaled automatically to the computer program. This avoids an erroneous test measurement.

After the second step, the computer program may issue a prompt to substitute and mount a different phantom on the platform, with the aforementioned additional X-ray absorption distribution being obtained with the different phantom on the platform. Substitution of phantoms may be necessary in particular test measurements or calibrations, specifically during production.

In another embodiment, the phantom in use is identified automatically based on specified characteristics, and a specified program may be chosen depending on the identification of the phantom. For example, the specified characteristics may be a specified absorption pattern. The phantom may also be identified by the computer program by other characteristics, such as a bar code or movement of a mechanical switch during insertion of the phantom. Depending on the identification of the phantom, the corresponding test measurement may then be undertaken.

In a further embodiment, the predetermined Z-position of the phantom is automatically adjusted by movement of the platform controlled by the computer program. Manual adjustment of the Z-position of the phantom, as is conventional, is no longer required. This facilitates a particularly precise test measurement.

It is also advantageous to use the procedure for test measurements in an automated procedure to calibrate the X-ray computed tomography apparatus. In this case, a first parameter set can be calibrated after the measurement in the second step, and a second set can be calibrated after the measurement in the third step. The calibrated parameter sets are used in the control of the X-ray computed tomography apparatus and influence the computed reconstruction of the views. "Calibration" is defined in the present invention as the setting or adjustment of an X-ray computed tomography apparatus in order to produce the most precise views obtainable. To that end, pre-specified parameter sets are redefined or updated based on X-ray absorption distribution patterns measured by use of the phantom.

In a further embodiment the computer program determines the order of measurement and/or calibration according to a pre-specified algorithm. In other words, the computer program determines all necessary movements of the platform and thus of the segments of the phantom to be scanned depending on the current calibration requirements. It also determines the order of the various steps. It is most advantageous that the parameters required for the current measurement and/or calibration are selected and transferred automatically. Such parameters may be stored in pre-specified tables to be retrieved automatically by the computer program depending on the calibration requirements at issue and the selected phantom.

The above object also is achieved in accordance with the invention by an X-ray computed tomography apparatus with a data processing unit to handle the processing of the inventive method. The X-ray computed tomography apparatus includes a platform that is moveable with respect to the X-ray data acquisition unit, with a combined phantom containing several individual phantoms attached to the platform. The phantom may also be integrated into the platform by being incorporated into a bed attached to the platform, i.e. the user cannot substitute phantoms.

A computed tomography apparatus having a movable patient bed, which can serve as the platform for the phantom, is described in U.S. Pat. No. 6,470,065, the teachings of which are incorporated herein by reference.

DESCRIPTION OF THE PREFERRED EMBODIMENTS

Figure 1:
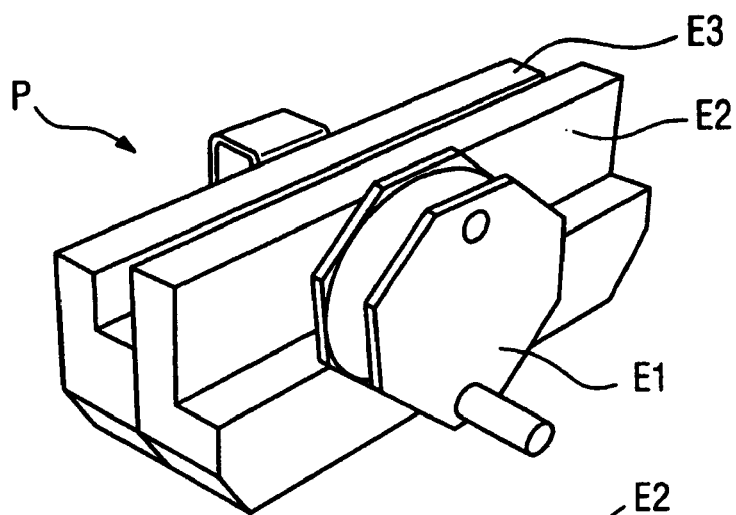
FIG. 1 illustrates a first embodiment of combined phantom usable in the method and apparatus of the present invention.
Figure 2:
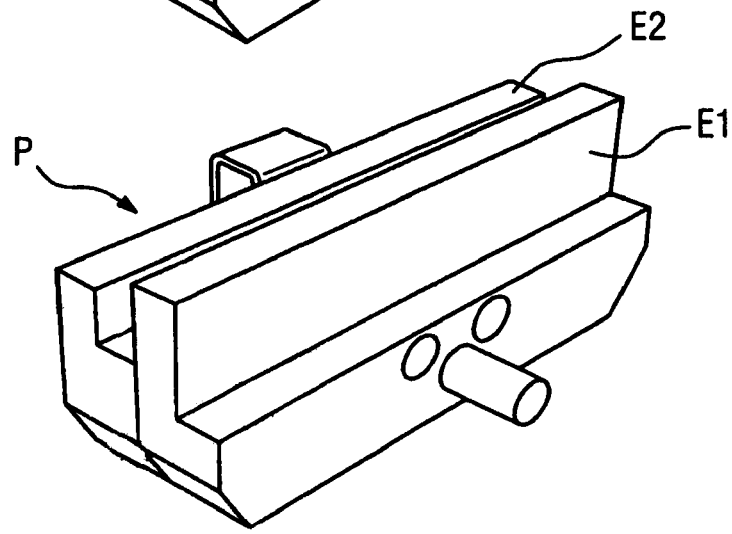
FIG. 2 illustrates a second embodiment of combined phantom usable in the method and apparatus of the present invention.
Figure 3:
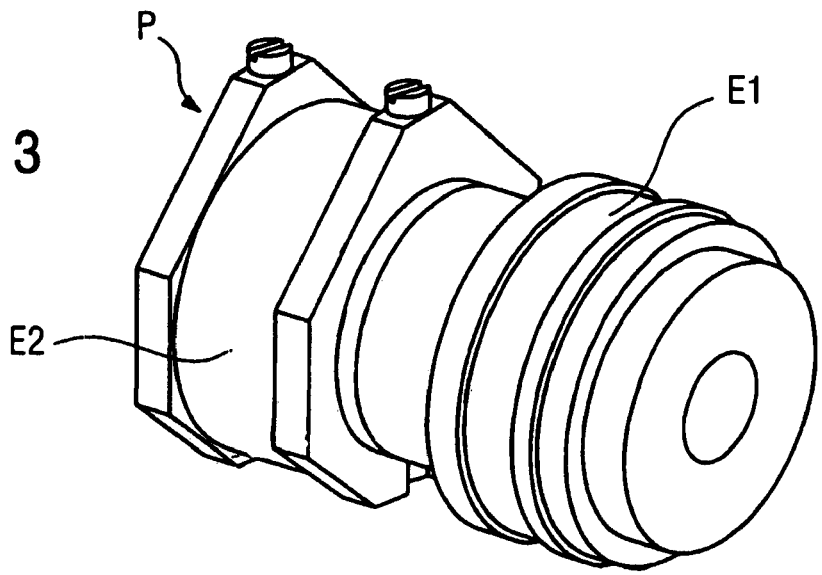
FIG. 3 illustrates a second first embodiment of combined phantom usable in the method and apparatus of the present invention.

The combined phantoms P shown in FIG. 1 to FIG. 3 are formed in each case of several individual phantoms E1, E2, and E3. Each of the individual phantoms E1, E2, and E3 forms a segment of phantom P. The individual phantoms E1, E2 and E3 are test specimens, which are particularly well suited to different calibration tasks.

The inventive procedure operates as follows, whenever a hardware component is replaced, for example:

As a first step, a calibration menu of the computer program is notified that a hardware component has been replaced. The computer program now displays a list of hardware components, from which the service technician selects the relevant replaced hardware component. The computer program then prompts the service technician to mount a specified phantom on the bed of the CT apparatus.

The computer program now checks either by reference to a survey (scout) measurement or other characteristics of the phantom, whether the correct phantom has been mounted on the berth. If that is true, the measurement of the phantom commences automatically. The computer program initially focuses on the first segment E1 of the phantom. Several sectional views are taken. The parameter sets to be calibrated are supplied automatically by the computer program and are calibrated by reference to the actual measurements. An algorithm contained in the computer program then moves the berth into the measurement position for the next segment of the phantom. Additional views are obtained. A second parameter set is calibrated based on the measurements. Additional measurements of the phantom are taken, until all segments required for the calibration are measured. After the measurement procedure is completed, the service technician is notified that the phantom may be removed from the bed.

A further simplification of the procedure employs a phantom that is permanently installed in the platform or that is a component of the bed on the platform. If that is the case, then the steps of mounting and dismounting the phantom are omitted.

Figure 4:
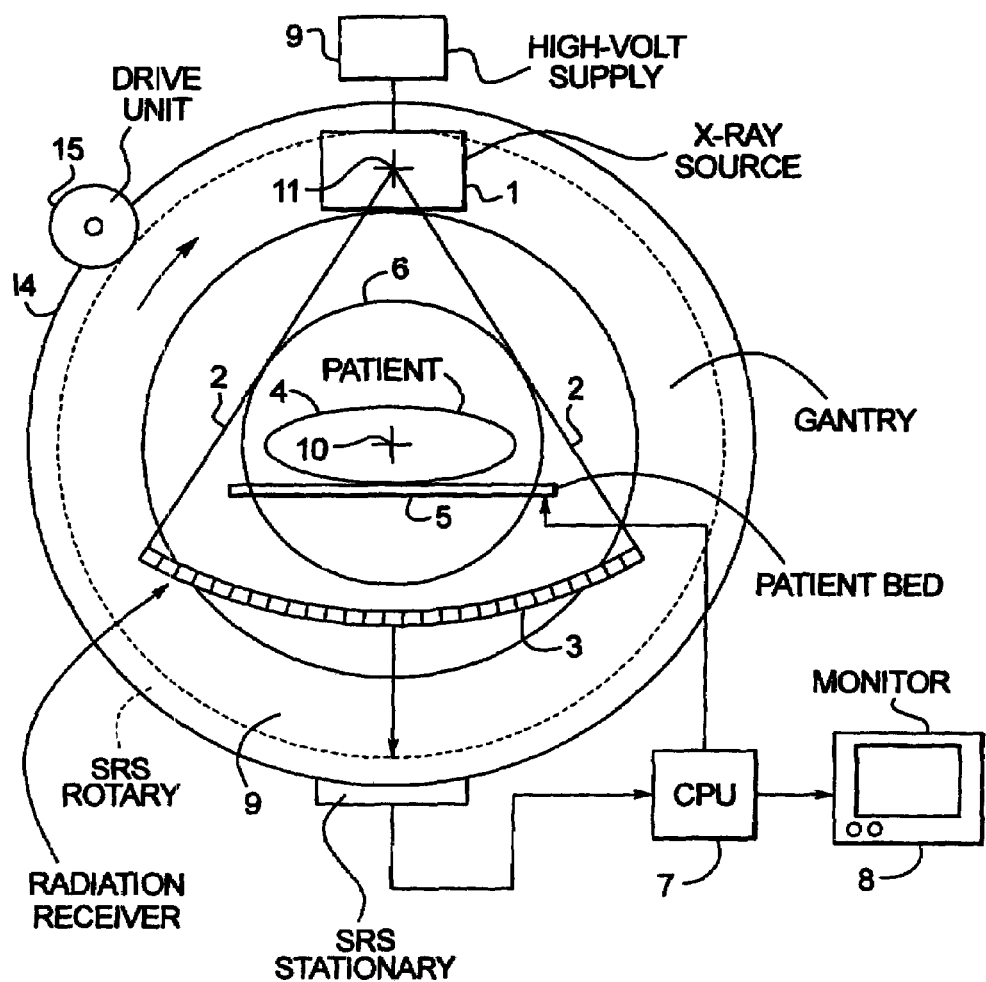
FIG. 4 schematically illustrates a computed tomography apparatus constructed and operating in accordance with the present invention.

The basic components of a CT system operating according to the present invention are depicted in FIG. 4. The CT system has an x-ray source 1 and a radiation receiver 3 that are mounted on a rotatable gantry 14. The x-ray source 1 is operated by a high voltage supply 9 to emit a fan-shaped x-ray beam 2 from a focus 11. The gantry 14 is rotated in the direction of the arrow by a drive unit 15 so that a patient 4, disposed in an examination volume 6 and lying on a patient bed 5, is irradiated by the x-ray beam 2 from a number of different projections. For each projection, measurement data are produced by the radiation receiver 3 dependent on the attenuated x-rays incident thereon., in the plane of the drawing shown in FIG. 4, the radiation receiver is shown as being composed of a row of detector elements, however, the x-ray beam and the radiation receiver 3 will have an extent perpendicular to the plane of the drawing such that the receiver 3 will be composed of a number of adjacent detector rows, such as four rows (four channels). Measurement data from the radiation receiver 3 are supplied to a slip ring system composed of a rotary module SRS rotary and a stationary module SRS stationary. The data are supplied to a central processing unit 7 for image reconstruction of the scanned object, which is displayed on a monitor 8.

In accordance with the present invention, the central processing unit 7 also controls movement of the patient bed in the manner described above, with a phantom as described above disposed on the patient bed 5.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for making for test measurements in an x-ray computed tomography apparatus, comprising the steps of:
providing a combined phantom having a specified characteristic associated therewith, said phantom consisting of a plurality of individual phantoms, each individual phantom forming a segment of the combined phantom, and affixing the combined phantom to a platform that is movable with respect to a data acquisition unit of a computed tomography apparatus;
automatically controlling movement of said platform with a control unit loaded with a computer program comprising a plurality of different routines for obtaining x-ray absorption distributions, and in said control unit executing said computer program, automatically recognizing said specified characteristic of said phantom and selecting one of said routines dependent on said specified characteristic;
in said one of said routines, automatically moving said platform with said combined phantom affixed thereto into a predetermined first position with respect to said data acquisition unit and obtaining a first x-ray absorption distribution in a first segment of said combined phantom with said data acquisition unit;
in said one of said routines, automatically moving said platform with said combined phantom affixed thereto from said first position into a second predetermined position and obtaining a second x-ray absorption distribution of a different segment of said combined phantom with said data acquisition unit.

2. A method as claimed in claim 1 wherein said x-ray computed tomography apparatus includes a display, and comprising the additional step of issuing a prompt at said display from said computer program to affix said combined phantom to said platform.

3. A method as claimed in claim 1 comprising, in said computer program, automatically confirming that said combined phantom is correctly affixed to said platform.

4. A method as claimed in claim 1 wherein said computed tomography apparatus comprises a display, and comprising the additional step of issuing a prompt from said computer program at said display after obtaining said first x-ray absorption distribution to remove said combined phantom from said platform and to affix a different phantom to said platform for obtaining said second x-ray absorption distribution.

5. A method as claimed in claim 1 wherein said data acquisition unit has a unit axis along which said platform is moved, and comprising automatically controlling, with said computer program, movement of said platform along said axis.

6. A method as claimed in claim 1 comprising calculating a first parameter set from said first x-ray absorption distribution and calculating a second parameter set from said second x-ray absorption distribution.

7. A method as claimed in claim 1 comprising automatically controlling said sequence with a predetermined algorithm in said computer program.

8. A method as claimed in claim 1 comprising, in said computer program, automatically deriving respective parameters from said first and second x-ray absorption distributions, and employing said parameters for subsequently obtaining a diagnostic image of an examination subject with said data acquisition unit.

9. A method as claimed in claim 1 wherein said specified characteristic is a specified absorption pattern of said combined phantom, and wherein the step of automatically recognizing said combined phantom comprises automatically recognizing said combined phantom from said specified absorption pattern.

10. An x-ray computed tomography apparatus comprising:
a CT data acquisition unit for emitting and detecting x-rays;
a platform that is movable relative to said CT data acquisition unit;
a combined phantom consisting of a plurality of individual phantoms, each individual phantom forming a segment of said combined phantom, said combined phantom being affixed to said platform, said phantom having a specified characteristic; and
a control unit for controlling movement of said platform and operation of said CT data acquisition unit automatically with a computer program comprising a plurality of different routines for obtaining x-ray absorption distributions, said control unit, in said computer program, automatically recognizing said specified characteristic of said phantom and selecting one of said routines dependent on said specified characteristic and said control unit, in said one of said routines, automatically moving said platform to a first position and obtaining a first x-ray absorption distribution of a first segment of said combined phantom with said CT data acquisition unit, and automatically moving said platform from said first position to a second position and for obtaining a second x-ray absorption distribution of a second segment of said combined phantom with said CT data acquisition unit.

11. An x-ray computed tomography apparatus as claimed in claim 10 wherein said combined phantom is affixed to said platform by integration into said platform.

12. An x-ray computed tomography apparatus as claimed in claim 10 wherein said phantom has an absorption pattern forming said specified characteristic, and wherein said control unit recognizes said combined phantom from said specified absorption pattern.

* * * * *